United States Patent [19]

Szikriszt

[11] Patent Number: 4,836,918

[45] Date of Patent: Jun. 6, 1989

[54] APPARATUS FOR GAS-PRODUCING TREATMENT OF ORGANIC MATERIAL

[76] Inventor: Georg Szikriszt, Badstrandsvägen 12, S-112 65 Stockholm, Sweden

[21] Appl. No.: 933,223

[22] PCT Filed: Mar. 7, 1986

[86] PCT No.: PCT/SE86/00097

§ 371 Date: Nov. 5, 1986

§ 102(e) Date: Nov. 5, 1986

[87] PCT Pub. No.: WO86/05171

PCT Pub. Date: Sep. 12, 1986

[30] Foreign Application Priority Data

Mar. 8, 1985 [SE] Sweden ................................ 8501166
Mar. 8, 1985 [SE] Sweden ................................ 8501167

[51] Int. Cl.⁴ ........................... C02F 11/04; B01F 9/06
[52] U.S. Cl. ..................................... 210/151; 210/180; 210/188; 210/404; 210/539; 435/303; 435/306; 435/312
[58] Field of Search ............... 210/603, 619, 784, 179, 210/180, 150, 151, 188, 210-217, 402-404, 521, 522, 523, 539; 435/303, 801, 813, 306, 312

[56] References Cited

U.S. PATENT DOCUMENTS

| | | | |
|---|---|---|---|
| 3,540,589 | 2/1970 | Boris | 210/150 |
| 3,630,893 | 12/1971 | Tanaka et al. | 210/210 X |
| 3,720,320 | 3/1973 | Fletcher | 210/210 X |
| 3,779,911 | 12/1973 | Freudenthal et al. | 210/213 X |
| 4,038,184 | 7/1977 | Svanteson | 210/180 X |
| 4,541,929 | 9/1985 | Janusch | 210/217 |

FOREIGN PATENT DOCUMENTS 3343444 6/1984 Fed. Rep. of Germany.
8005865-4 2/1982 Sweden.
8306508-6 5/1985 Sweden.

Primary Examiner—Tom Wyse
Attorney, Agent, or Firm—Hill, Van Santen, Steadman & Simpson

[57] ABSTRACT

Apparatus for gas-producing treatment, particularly fermentation and digestion, of organic material contained in a suspension comprises a horizontal, rotatably mounted treatment drum having an inlet for the suspension at one end and an outlet for the treated suspension at the other end. A plurality of baffles extending in axial planes throughout the length of the drum are secured to the interior side of the drum and extend from there towards the central region of the drum. In each of a number of angular drum positions, the number being equal to the number of baffles, one of the baffles defines jointly with the wall of the drum a downwardly open gas collection space which is spaced from the vertical plane containing the axis of rotation of the drum. The gas collected therein causes an uneven distribution of the suspension within the drum and thereby causes a turning moment acting on the drum. Guide ribs secured to the baffles and the interior side of the drum wall cause, by virtue of the rotation of the drum, axial transport of sediment and float material layer towards the outlet.

12 Claims, 3 Drawing Sheets

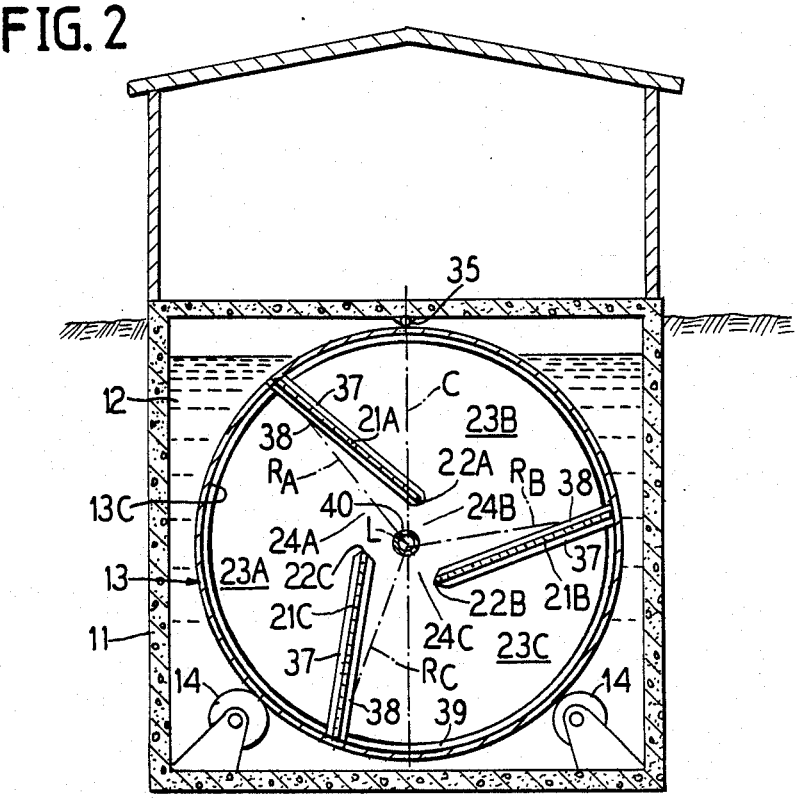
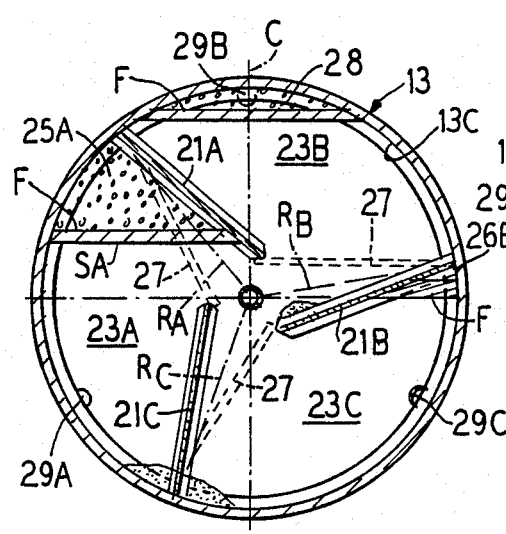
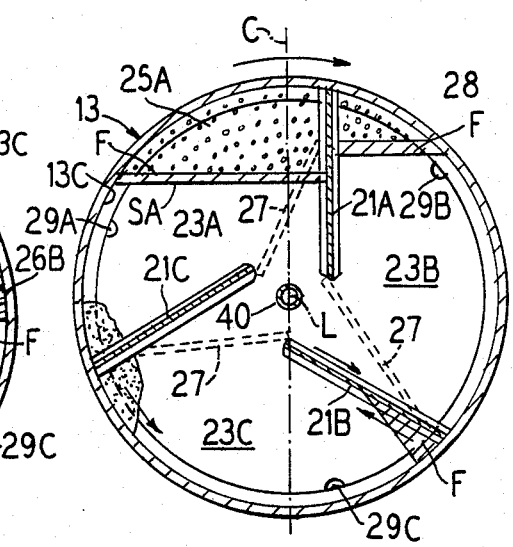

APPARATUS FOR GAS-PRODUCING TREATMENT OF ORGANIC MATERIAL

This invention relates to apparatus for gas-producing treatment, especially fermentation or digestion, of organic material.

Accordingly, the apparatus according to the invention comprises a horizontal treatment drum adapted to be rotated about its horizontal axis and material transport means fixedly secured to the drum interiorly thereof.

Particularly when the material to be treated is industrial or domestic waste, it often includes a substantial portion of solid materials that are not biodegradable. Such materials may be both heavy materials, such as sand, pebbles, metal objects, having a tendency to separate from the suspension by settling, and light materials tending to rise to and float on the surface of the suspension and form a so-called scum layer.

An object of the invention is to provide in apparatus of the afore-mentioned kind a treatment drum capable of transporting undegradable material through the drum more rapidly than the remaining, degradable material which requires a certain, relatively long retention time within the drum.

To this end, in apparatus according to the invention, the material transport means comprises a plurality of guide ribs which are spaced longitudinally of the drum and include an acute angle with transverse planes through the drum and which are attached to axially extending support surfaces fixed with respect to the drum, the guide ribs being arranged such that settling particles in the drum intercepted by a flank of the guide ribs are deflected thereby towards the other end of the drum.

As will appear more clearly from the following detailed description, the invention makes use of the idea of utilizing the vertical motion of material tending to separate from the suspension and, by redirecting this movement towards the outlet end of the drum by means of guide ribs, effecting transport of such material towards the outlet end while the drum rotates.

In apparatus of the kind to which the invention relates the drum may be very large; the volume of the drum may be ten thousand cubic meters or more in the case of apparatus for digestion of industrial, domestic or agricultural wastes. Even if the drum is immersed in water so that the load on the drum support devices is moderate, the turning moment required for the rotation is great. The drive means therefore has to be dimensioned to produce substantial forces and apply them to the drum and for this reason is expensive.

Accordingly, a further object of the invention is to substantially reduce or more or less eliminate the driving force that has to be applied externally to the drum to rotate it.

This aspect of the invention is based on the idea of utilizing the gas produced during the treatment (in the case of digestion chiefly methane and carbon dioxide) to effect an uneven distribution within the drum of the material being treated therein such that the material applies to the drum a turning moment acting in the desired direction of rotation of the drum.

To this end, in apparatus according to the invention, in each of a plurality of angular drum positions baffles provided within the drum define together with the interior side of the drum a downwardly open gas collection space which is spaced from the vertical plane containing the axis of rotation of the drum.

In this space the produced gas, or at least a substantial portion thereof, is collected during the treatment. The collected gas prevents the fluid or slurry-like material in the drum from distributing itself evenly on both sides of the vertical plane containing the axis of rotation. As a consequence, a larger portion of the material will be present on the side of the vertical plane remote from the gas collection space and the material will thus apply to the drum a resulting turning moment tending to turn the drum such that the gas collection space and the adjoining parts of the drum are lifted.

Suitably, the drum is rotated intermittently. The apparatus then may include a control device which arrests the drum in each of the afore-said rotational positions, which may be angularly spaced apart 90 or 120 degrees, for example.

The invention is explained in greater detail hereinafter with reference to the accompanying diagrammatic drawings.

FIG. 2 is a cross-sectional view of the apparatus of FIG. 1;

Figure 1:
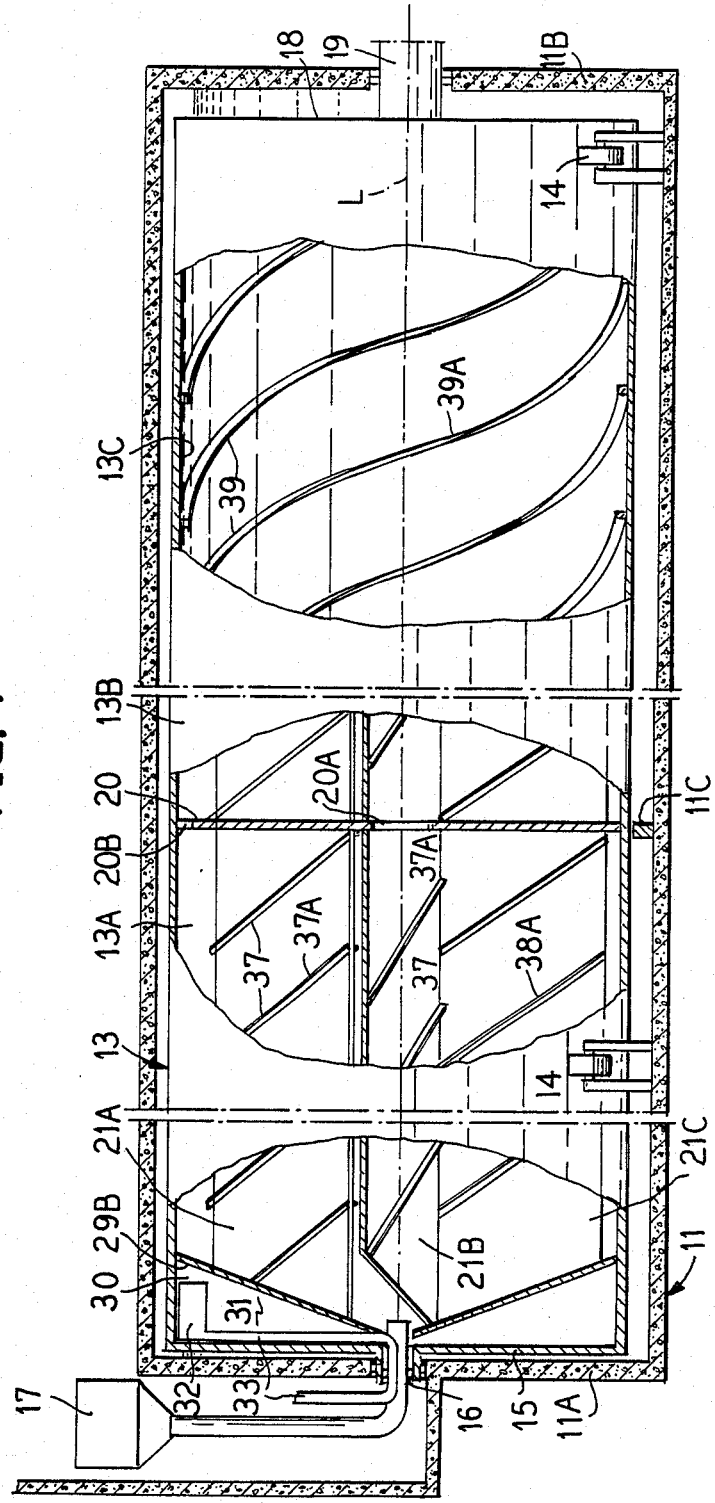
FIG. 1 is a side elevation, with portions broken away, of treatment apparatus, namely digestion apparatus, embodying the invention.
Figure 5:
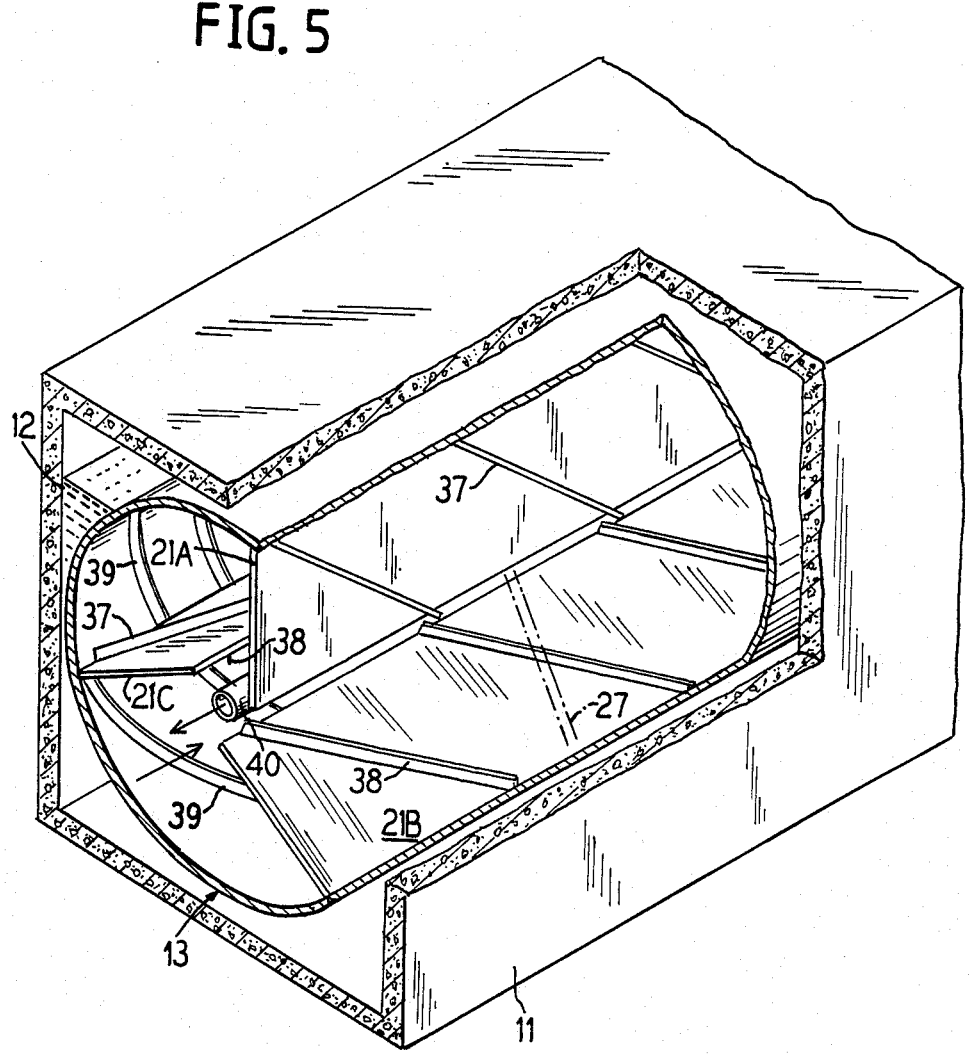

FIGS. 3 and 4, which are cross-sectional views showing the treatment drum respectively in a dwell position and during rotational movement between two dwell positions, illustrate the manner in which the drum is rotated;

FIG. 5 is a perspective view with portions broken away and illustrates means for effecting axial transport of both sediment and the scum layer.

As shown in the drawings, the apparatus comprises a housing 11, e.g. of concrete, almost completely filled with temperature-controlled water 12. Enclosed within the housing 11 is a digester tank in the shape of a horizontal circular cylindrical drum 13 which is almost completely immersed in the water and is supported for rotation about its horizontal axis L by a number of support rollers 14. Centrally of one end wall 15 the drum 13 has an inlet tube 16 connected through a swivel coupling with a device 17 for continuously or intermittently feeding the material to be digested into the drum. This material is mainly an aqueous suspension or slurry of organic substances but may also include inorganic, indigestable solid material. Centrally of the other end wall 18 of the drum an outlet tube 19 for the digested material is provided. Both the inlet tube 16 and the outlet tube 19 are sealingly journalled in the end walls 11A and 11B of the housing 11.

Disregarding the inlet and outlet tubes in the end walls 15 and 18, the drum—which may be made of plastic, sheet metal or concrete, for example—is closed.

A transverse partition 20 divides the interior of the drum 13 into two compartments communicating with one another through openings in the partition, a central opening 20A and small openings 20B near the periphery. A partition 11C provides a corresponding division of the housing 11. The two housing compartments may hold water of different temperatures so that the material contained in the drum compartments 13A and 13B is kept at different temperatures. Naturally, the drum and the housing may be divided into more than two compartments.

The central opening 20A in the transverse drum partition 20 permits transfer of material from the drum compartment 13A into the drum compartment 13B.

Provided within the drum 13 and extending over substantially the entire length of the drum are also three flat baffles 21A, 21B, 21C which are fixedly secured to the interior side 13C of the drum and are circumferentially spaced apart 120 degrees. As best shown in FIGS. 3 and 4, the width of the baffles is almost equal to the radius of the drum, but because the radially inner, free edges 22A, 22B, 22C of the baffles are displaced unidirectionally from the radii $R_A$, $R_B$, $R_C$ passing through the rotational axis L and the respective radially outer longitudinal baffle edges where the baffles are secured to the drum, the three drum regions 23A, 23B, 23C between adjacent baffles 21A, 21B, 21C are in open communication with one another.

The width of the open passages or gaps 24A, 24B, 24C between adjacent inner edges of the baffles 21A, 21B, 21C is not critical but suitably is 0.2 to 0.6 times the internal drum radius. Similarly, the width of the baffles, that is the distance between their radially outer edge where they are secured to the interior side 13C of the drum and their radially inner, free edge 22A-22C, is not critical but suitably is not less than 0.5 times the internal drum radius.

The drum is supported to rotate intermittently in angular steps of 120 degrees, so that each full revolution comprises three successive steps. A control device, not shown, divides the rotational movement into the 120 degrees steps. All, or at least the major portion of the motive power for the rotational movement is produced by the material being treated in the drum, namely as a consequence of an "unbalancing" or uneven distribution of the material which is caused by the gas produced in the course of the digestion process as will be explained below with reference to FIGS. 3 and 4.

FIG. 3 shows the state in which the drum 13 is in one of the three dwell positions.

During the period when the drum 13 is in the dwell position shown in FIG. 3, the major portion of the digestion gas produced in the left-hand half of the drum 13, that is, within the digesting material situated below the baffle 21A, is collected in a gas collection space 25A which is limited in the upward direction and laterally by the interior side 13C of the drum 13 and by the baffle 21A and is limited in the downward direction by the horizontal surface SA of the digesting material extending between the interior side o the drum and the baffle 21A, i.e. by the scum layer F.

During the dwell period the volume of the gas collected and trapped in the gas collection space 25A increases gradually so that the lower limiting surface SA is gradually depressed.

Similarly, the gas produced in the digesting material situated below the baffle 21B is collected in a gas collection space 26B. However, the volume of gas produced in the material below the baffle 21B is smaller than the volume of gas produced in the material below the baffle 21A (the amount of material is smaller) and, besides, the gas in the space 26A is transferred to the space 25A through a number of transfer tubes 27 provided at suitable intervals along the entire length of the drum.

The rest of the digestion gas produced in the drum rises to a space 28 at the top of the drum from which the gas is discharged through a gas discharge opening 29B near the periphery of the drum adjacent the end wall 15.

In the illustrated dwell position the gas discharge opening 29B is in open communication with a gas discharge space 30 at the top portion of an end chamber 31 immediately inwardly of the drum end wall 15. This end chamber, which is always in open communication with further peripheral gas discharge openings 29A and 29C, is filled to a substantial degree with the digestion material. Within the gas discharge space 30 there is a gas discharge hood 32 connected to a gas storage chamber (not shown) through a conduit 33 passed through the inlet tube 16.

As apparent from FIG. 3, the collection of gas in the gas collection space 25A during the dwell period will cause an uneven or unbalancing distribution of the digestion material between the portions of the drum situated on opposite sides of the vertical plane C containing the rotational axis L of the drum. As a consequence, the digestion material will cause a resulting turning moment acting on the drum and tending to rotate it clockwise as viewed in FIG. 3.

However, the control device already mentioned prevents. rotation of the drum until a certain time has elapsed and/or until the turning moment has reached a certain value or until a certain other condition is met.

When this condition is met, the drum is allowed to rotate through 120 degrees so that the baffle 21A takes the position in which the baffle 21B was during the preceding dwell period, the baffle 21B takes the position in which the baffle 21C was during the proceding dwell period, and the baffle 21C takes the position in which the baffle 21A was during the preceding dwell period. The gas in the gas collection space 25A is discharged through the gas discharge opening 29A which, following the rotational movement, is at the top of the drum. The above-described process is then repeated.

The rotational movement of the drum is relatively rapid and results in a correspondingly rapid agitation and thorough mixing of the digestion material contained in the drum. The agitation facilitates a separation of certain solid, light portions of the material. Such portions, which rise to the scum layer F because of their buoyancy and thus float on the surface of the suspension in the drum, may be, for example, pieces of plastic film and other kinds of lightweight material frequently contained in domestic waste.

The above-described self-rotation of the drum 13 may eliminate completely or almost completely the need for external driving of the drum during normal operation. Nevertheless it may be advisable to provide the apparatus with a separate drive unit which can be used when it is necessary to apply an external turning moment to the drum. Application of an external turning moment may be necessary for example during startup or shutdown of the apparatus when the drum is only partially filled with digestable material or in other situations when the gas production is insufficient. The drive unit may be much smaller, simpler and cheaper in such a case than when it has constantly to supply all the power required to rotate the drum. A drive unit of the above-indicated auxiliary type is diagrammatically shown in FIG. 2 and designated by numeral 35. It is combined with the above-mentioned control unit.

In addition to forming part of the drum drive system, the baffles 21A, 21B, 21C form part of a material transport system in the drum 13. To this end, both sides of the baffles are provided with upstanding ribs 37, 38 extending from the interior side 13C of the drum to the free, radially inner longitudinal baffle edges 22A-22C.

The ribs on each side are substantially straight and parallel and include an acute angle with the parallel longitudinal edges of the baffles and thus with a plane perpendicular to the axis of the drum. The ribs 37 on the baffle side directed in the direction of rotation of the drum 13—the drum rotates clockwise, viewed as in FIGS. 2 to 5—are disposed such that when viewed from the interior side 13C of the drum towards the radially inner, free longitudinal edge of the associated baffle, each rib extends obliquely towards the outlet end of the drum. On the other hand, the ribs 38 on the opposite baffle side are disposed such that they extend obliquely away from the outlet end of the drum when viewed from the interior side of the drum towards the radially inner, free longitudinal edge of the associated baffle.

The material transport system also comprises a number of ribs 39 fixedly secured to and upstanding from the interior side 13C of the drum with each rib extending along a left-hand helix. These ribs 39 are provided over substantially the entire axial length of the drum and extend over substantially the entire periphery of the drum.

Primarily, the material transport system formed by the baffles 21A, 21B, 21C and the ribs 37, 38, 39 serves the purpose of effecting a rapid transport through the drum of material having a tendency to settle in the drum, such as sand, pebbles, metal objects and other materials which are not biodegradable and which should therefore remain in the drum as short a time as possible. For convenience, such materials are hereinafter termed settling materials or sediment. Materials having a tendency to float on top of the suspension and thus to form part of the scum layer F are also rapidly transported through he drum by the action of the ribs 38.

The operation of the material transport system is explained below with reference to FIGS. 3 to 5.

During the dwell period when the drum is in the position shown in FIG. 3, the settling materials slowly fall towards the lowermost part of the drum, a portion of the material being intercepted by the baffle 21A, another portion being intercepted by the baffle 21B, a further portion being intercepted by the segment of the interior side 13C of the drum 13 extending between the baffles 21B and 21C and a still further portion being intercepted by the segment of the interior surface of the drum situated to the left of the baffle 21C. A smaller or larger portion of the sediment intercepted by the baffle 21A slides towards the free longitudinal edge 22A of the baffle 21A and simultaneously is moved towards the outlet end of the drum by the side or flank 38A of the ribs 38 which is directed towards the outlet end. When reaching the free longitudinal edge 22A of the baffle 21A, some of this material falls to the baffle 21B and is intercepted by this baffle adjacent its free longitudinal edge 22B. From there, some of the material may fall to the lowermost portion of the interior side of the drum adjacent the vertical plane C.

When the drum is rotated clockwise one-third of a full turn towards and through the position shown in FIG. 4 to the next dwell position, the continued operation is as follows.

Any sediment remaining on the baffle 21A slides off from it in the above-described manner and consequently is also moved towards the outlet end of the drum by the side or flank 37A of the ribs 37. When this sediment reaches the baffle 21B, it will slide towards the interior side 13C of the drum together with any sediment already intercepted by the baffle and, during this sliding movement the sediment will be deflected through an additional distance towards the outlet end of the drum by the side or flank 38A of the ribs 38 which faces the outlet end. The sediment then temporarily remains adjacent the interior side of the drum.

During or after the rotation, most of the sediment intercepted by the interior side of the drum between the baffles 21B and 21C will move along the interior side towards the portion of the drum that is lowermost at the moment. At the same time, this sediment will be moved towards the outlet end of the drum by the flank or side 39A of the ribs 39 facing the outlet end of the drum.

During the rotation, the sediment intercepted by the interior side of the drum on the clockwise side of the baffle 21C will be carried along until the baffle 21C is in the position occupied by the baffle 21A in the position shown in FIG. 3. When the baffle 21C reaches that position, at least a portion of this sediment can start moving on the baffle 21C towards the center of the drum, the sediment being then also deflected towards the outlet end of the drum by the flanks 37A of the ribs 37 on the baffle.

During the rotation, the portion of the scum layer F trapped below the baffle 21B will also slide upwardly along the underside of the baffle (see FIG. 4), the flanks 37B of the ribs 37 deflecting this portion of the scum layer towards the outlet end of the drum until it moves off from the baffle 21B at the free edge 22B thereof and rises to the uppermost portion of the drum.

During the dwell period following the rotation and the subsequent further rotation (following which the drum has rotated two-thirds of a full turn), the above-described separation and transportation steps are repeated and they are then repeated again during each subsequent dwell period and rotation.

From the foregoing explanation it is apparent that the major portion of the sediment and a smaller or larger portion of the scum layer F are moved towards the outlet end of the drum in connection with each rotation of the drum. A particle or body of settling material or a light particle entering the drum 13 at the inlet end can thus move through the drum in a time that is short in comparison with the retention time for the major portion of the suspension in the drum.

Naturally, the ribs 37,38 on each baffle should be arranged in such a way relative to the ribs on the other baffles and the ribs 39 on the interior side of the drum that the largest possible portion of the length of each rib is utilized for the axial transport. The height of the ribs 37, 38 is not critical; it may be, for example 0.01-0.05 times the radius of the drum.

Adjacent the outlet end of the drum the shapes of the baffles 21A-21C and the ribs 37-39 are modified in a manner not shown such that the sediment and the scum layer F are directed into the outlet tube 19 and carried out of the drum 13 to a recipient compartment not shown within or adjacent the housing 11. The digested material is also discharged into this recipient compartment from the drum 13. Near the transverse partition 20 in the drum the shapes of the baffles and the ribs are likewise modified such that the sediment ad the float material layer F are carried to and through the central opening in the partition.

A recycling tube 40 extends along the axis of the digester drum 13 to recycle, in a manner not shown, a small portion of the fully digested or almost fully digested material from a location near the outlet end of the drum to a location near the inlet end. The recycled material acts as an inoculant for the freshly fed material to accelerate the digestion thereof.

In the illustrated exemplary embodiment described above, there are three baffles 21A–21C with uniform angular spacing. This has been found to be preferable, at least in certain cases. However, it is within the scope of the invention to provide a different number of baffles and to shape and arrange them in a manner different from that shown and described. For example, the baffles may be curved or angled in different ways in cross-section and the angle they include with the radius $R_A$, $R_B$, $R_C$ extending through their radially outer longitudinal edge may vary within wide limits. In the exemplary embodiment, the baffles are offset in the direction of rotation from this radius $R_A$, $R_B$, $R_C$, but if desired they may be offset in the opposite direction. Preferably, the angle included between the baffles and the respective radii is not more than $+/-30$ degrees.

Naturally, the above-described material transport system is useful also in the case where the drum is rotated continuously or intermittently in very small steps. It is also useful in the case where the drum is rotated by an external drive system. Moreover, the above-described arrangement for causing rotation of the drum can be used independently of the material transport system.

I claim:

1. Apparatus for gas-producing treatment, especially fermentation or digestion, of organic material contained in a liquid suspension, comprising an elongated horizontal treatment drum which is rotatable about its axis and which has a material inlet at one end, a material outlet at the other end, a plurality of baffles extending axially of the drum, each baffle having front side and an opposite side and being fixedly secured to the interior circumferential side of the drum and projecting therefrom towards the opposite side of the drum and material transport means comprising a plurality of guide ribs spaced apart longitudinally of the drum and including an acute angle with a transverse drum plane, said ribs being secured to said front side of each baffle and arranged such that particles settling in the drum and intercepted by a flank of the guide ribs are deflected towards the said other end of the drum by the flank.

2. Apparatus according to claim 1 wherein a further group of the guide ribs is secured to the interior circumferential surface of the drum.

3. Apparatus according to claim 1 wherein a further plurality of guide ribs, which are spaced apart longitudinally of the drum and including an acute angle with a transverse drum plane, are fixedly secured to said opposite side of the baffles and are arranged such that particles settling in the drum and intercepted by a flank of said further guide ribs are deflected towards said other drum end by this flank.

4. Apparatus according to claim 1 wherein the baffles and the guide ribs adjacent said other end are adapted also to deflect the particles towards the central region of the drum.

5. Apparatus for gas-producing treatment, especially fermentation or digestion, of organic material contained in a liquid suspension, comprising an elongated horizontal treatment drum which is rotatable about its axis, means for introducing and discharging the suspension and for collecting gas produced in the drum, and baffles mounted in the drum, said baffles in each of a plurality of angular drum positions defining together with the interior circumferential side of the drum a gas collection space which is spaced from the vertical plane containing the axis of the drum and which is open downwardly.

6. Apparatus according to claim 5, wherein the baffles are fixedly mounted in axial planes spaced from the axis of the drum and extend from the interior side to an axial line the distance of which from the interior side of the drum is at least 0.5 times the radius of the drum.

7. Apparatus according to claim 6 wherein the baffles extend substantially over an entire length of the drum.

8. Apparatus according to claim 6 wherein there are three baffles that are uniformly spaced circumferentially.

9. Apparatus according to claim 6, including conduit means for transferring to the gas collection space gas produced at the side of the vertical plane containing the axis of the drum which is remote from the gas collection space.

10. Apparatus according to claim 6, including means for temporarily arresting the drum in each of said angular positions.

11. Apparatus according to claim 6, wherein the said angular positions and the baffles are equal in number and uniformly spaced circumferentially.

12. Apparatus according to claim 6, wherein all baffles include an angle with the horizontal in each of said angular positions.

* * * * *